(12) United States Patent
Takayasu et al.

(10) Patent No.: US 6,194,588 B1
(45) Date of Patent: Feb. 27, 2001

(54) METHOD FOR PRODUCTION OF MALEIC ANHYDRIDE

(75) Inventors: Osamu Takayasu, Toyama-ken; Akiyoshi Nakajima; Hideto Hashiba, both of Hyogo-ken, all of (JP)

(73) Assignee: Nippon Shokubai Co., Ltd. (JP)

( * ) Notice: Subject to any disclaimer, the term of this patent is extended or adjusted under 35 U.S.C. 154(b) by 0 days.

(21) Appl. No.: 09/251,242

(22) Filed: Feb. 16, 1999

(30) Foreign Application Priority Data

Feb. 18, 1998 (JP) .................................................. 10-036198

(51) Int. Cl.$^7$ ......................... C07D 307/62; B01J 27/198
(52) U.S. Cl. ............................................. 549/259; 502/209
(58) Field of Search ............................. 549/259; 502/209

(56) References Cited

U.S. PATENT DOCUMENTS

| | | | |
|---|---|---|---|
| 3,864,280 | 2/1975 | Schneider | 502/209 |
| 4,231,943 | 11/1980 | Paradis et al. | 549/259 |
| 4,392,986 * | 7/1983 | Yang et al. | 252/435 |
| 4,855,459 | 8/1989 | Mummey | 502/209 |
| 5,070,060 | 12/1991 | Barone | 549/259 |
| 5,430,181 | 7/1995 | Arpentinier et al. | 562/406 |
| 5,530,144 | 6/1996 | Tsurita et al. | 502/259 |
| 5,773,382 * | 6/1998 | Mitchell et al. | 502/209 |

FOREIGN PATENT DOCUMENTS

| | | |
|---|---|---|
| 0029317 | 10/1980 | (EP) . |
| 044969 | 3/1982 | (JP) . |
| 59-132938 | 1/1983 | (JP) . |
| 05115783 | 10/1991 | (JP) . |
| 7171398 | 12/1993 | (JP) . |
| 093053 | 4/1995 | (JP) . |

OTHER PUBLICATIONS

Cataysis Today 28 (1996) pp. 139–145.
Journal of Catalysis 156, 28–36 (1995).
Journal of Catalysis, 140, 226–242 (1993).
Journal of Catalysis 145, pp. 256–266 (1994).

* cited by examiner

Primary Examiner—Bernard Dentz
(74) Attorney, Agent, or Firm—Omri M. Behr, Esq.

(57) ABSTRACT

In the production of maleic anhydride by the contact of a raw material gas containing an aliphatic hydrocarbon of not less than 4 carbon atoms and molecular oxygen with a vanadium-phosphorus oxide catalyst, the raw material gas is caused to allow presence therein of nitrogen and an inert gas possessing a thermal conductivity of not less than 800 ($10^{-4}Wm^{-1}K^{-1}$) at 700 K. The gas formed by the oxidation reaction is allowed to contact an absorbent to effect recovery of the produced maleic anhydride. Maleic anhydride is recovered from produced oxidation reaction gas separated from a remained oxidation reaction gas after recovering maleic anhydride, and the saparated inert gas is circulated to the reaction zone. The catalyst capable of producing maleic anhydride with a high yield can be obtained by activating the vanadium-phosphorus oxide catalyst with the gas composition containing an inert gas possessing a thermal conductivity of not less than 800 ($10^{-4}Wm^{-1}K^{-1}$) at 700 K.

10 Claims, 1 Drawing Sheet

METHOD FOR PRODUCTION OF MALEIC ANHYDRIDE

BACKGROUND OF THE INVENTION

1. Field of the Invention

This invention relates to a method for the production of maleic anhydride. More particularly, it relates to an improved method for the production of maleic anhydride by the catalytic gas phase oxidation of a raw material gas containing an aliphatic hydrocarbon of not less than 4 carbon atoms and molecular oxygen with a vanadium-phosphorus oxide catalyst. This invention further relates to a method for the activation of the vanadium-phosphorus oxide catalyst. More particularly, it relates to a method for the activation of a vanadium-phosphorus oxide catalyst suitable for the production of maleic anhydride by the catalytic gas phase oxidation of an aliphatic hydrocarbon of not less than 4 carbon atoms with a molecular oxygen-containing gas.

2. Description of the Related Art

It has been well known to produce maleic anhydride by subjecting an aliphatic hydrocarbon of not less than 4 carbon atoms such as, for example, n-butane, to gas phase oxidation in the presence of a vanadium-phosphorus oxide catalyst. Numerous patents have issued to inventions relating to vanadium-phosphorus oxide catalysts and reaction conditions to be used for the production.

As respects the oxidation reaction itself, the practice of selectively oxidizing n-butane, for example, into maleic anhydride by causing a raw material gas containing n-butane and molecular oxygen to contact a vanadium-phosphorus oxide catalyst has been prevailing (as disclosed in U.S. Pat. No. 3,864,280, JP-B-04-4,969, JP-A-05-115,783, U.S. Pat. No. 4,855,459, JP-A-09-3,053, JP-A-07-171,398, U.S. Pat. No. 5,530,144, and U.S. Pat. No. 5,070,060, for example).

This method, however, has been unable to produce the maleic anhydride with satisfactory conversion and selectivity.

Naturally an addition to the yield of the maleic anhydride as a target product brings such a commercial advantage as a reduction in cost. Thus, a further increase in the yield of maleic anhydride has been a constant study theme for researchers in this technical field.

An object of this invention, therefore, is to provide an improved method for the production of maleic anhydride.

Another object of this invention is to provide a method which, in the production of maleic anhydride by the gas phase oxidation of an aliphatic hydrocarbon of not less than 4 carbon atoms in the presence of a vanadium-phosphorus oxide catalyst, allows the maleic anhydride to be produced with a higher yield.

Still another object of this invention is to provide a method which allows effective utilization of an inert gas to be used in the reaction of oxidation.

Yet another object of this invention is to provide a method for the activation of a vanadium-phosphorus oxide catalyst which, in the production of maleic anhydride by the gas phase oxidation of an aliphatic hydrocarbon of not less than 4 carbon atoms in the presence of a vanadium-phosphorus oxide catalyst, allows the maleic anhydride to be produced with a higher yield.

SUMMARY OF THE INVENTION

The objects mentioned above are accomplished by the following items (1)–(11).

(1) A method for the production of maleic anhydride by the catalytic gas phase oxidation of a raw material gas containing an aliphatic hydrocarbon of not less than 4 carbon atoms and molecular oxygen with a vanadium-phosphorus oxide catalyst, characterized by the raw material gas allowing presence therein of nitrogen and an inert gas possessing a thermal conductivity of not less than 800 ($10^{-4}Wm^{-1}K^{-1}$) at 700 K.

(2) A method for the production of maleic anhydride by the catalytic gas phase oxidation of a raw material gas containing an aliphatic hydrocarbon of not less than 4 carbon atoms and molecular oxygen with a vanadium-phosphorus oxide catalyst, which comprises allowing presence in the raw material gas of nitrogen and an inert gas possessing a thermal conductivity of not less than 800 ($10^{-4}Wm^{-1}K^{-1}$) at 700 K thereby oxidizing the aliphatic hydrocarbon in the oxidizing reaction region, recovering maleic anhydride from the gas produced by the oxidation reaction, separating the produced maleic anhydride from a remained oxidation reaction gas after recovering the maleic anhydride, and circulating the separated inert gas to the reaction region.

(3) A method set forth in (1) or (2) above, wherein the total concentration of the nitrogen gas and the inert gas in the raw material gas is in the range of 60–94.5% by volume.

(4) A method set forth in any of (1) through (3) above, wherein the ratio of nitrogen gas to the inert gas (the molar ratio of nitrogen gas/inert gas) is in the range of 0.05/1–1/1.

(5) A method set forth in any of (1) through (4) above, wherein the inert gas is at least one species of inert gas selected from the group consisting of helium and neon.

(6) A method set forth in any of (1) through (5), wherein the inert gas is helium.

(7) A method set forth in any of (1) through (6), wherein the aliphatic hydrocarbon of not less than 4 carbon atoms is n-butane.

(8) A method for the activation of a vanadium-phosphorus oxide catalyst, characterized by activating the vanadium-phosphorus oxide catalyst with a gas composition containing an inert gas possessing a thermal conductivity of not less than 800 ($10^{-4}Wm^{-1}K^{-1}$) at 700 K.

(9) A method set forth in (8) above, wherein the gas composition contains nitrogen gas and the inert gas.

(10) A method set forth in (8) or (9) above, wherein the gas composition further contains an aliphatic hydrocarbon of not less than 4 carbon atoms and molecular oxygen.

(11) A method set forth in any of (8) through (10), wherein the activating temperature is in the range of 300°–600° C.

According to this invention, maleic anhydride aimed at can be produced with a high yield by causing the raw material gas to allow the presence therein of nitrogen and an inert gas possessing a thermal conductivity of not less than 800 ($10^{-4}Wm^{-1}K^{-1}$) at 700 K. Further, according to this invention, the maleic anhydride aimed at can be produced with a high yield by activating the vanadium-phosphorus oxide catalyst by the use of a gas composition resulting from the incorporation of nitrogen and an inert gas possessing a thermal conductivity of not less than 800 ($10^{-4}Wm^{-1}K^{-1}$) at 700 K in the raw material gas. The method provided by this invention for the production of maleic anhydride by the gas phase oxidation of an aliphatic hydrocarbon of not less than 4 carbon atoms with a molecular oxygen-containing gas in the presence of a vanadium-phosphorus oxide catalyst requires the presence of nitrogen and an inert gas possessing a thermal conductivity of not less than 800 ($10^{-4}Wm^{-1}K^{-1}$)

at 700 K at the reaction site and, at the same time, utilizes the inert gas entrained by the waste gas remaining after the recovery of the maleic anhydride by separating the inert gas from the waste gas and circulating the separated inert gas to the site of the reaction of oxidation. Thus, the method contemplated by this invention permits the inert gas such as, for example, helium which is relatively expensive to be utilized inexpensively and efficiently and, at the same time, allows the maleic anhydride to be produced with a high yield and at a low cost.

DESCRIPTION OF THE PREFERRED EMBODIMENT

Figure 1:
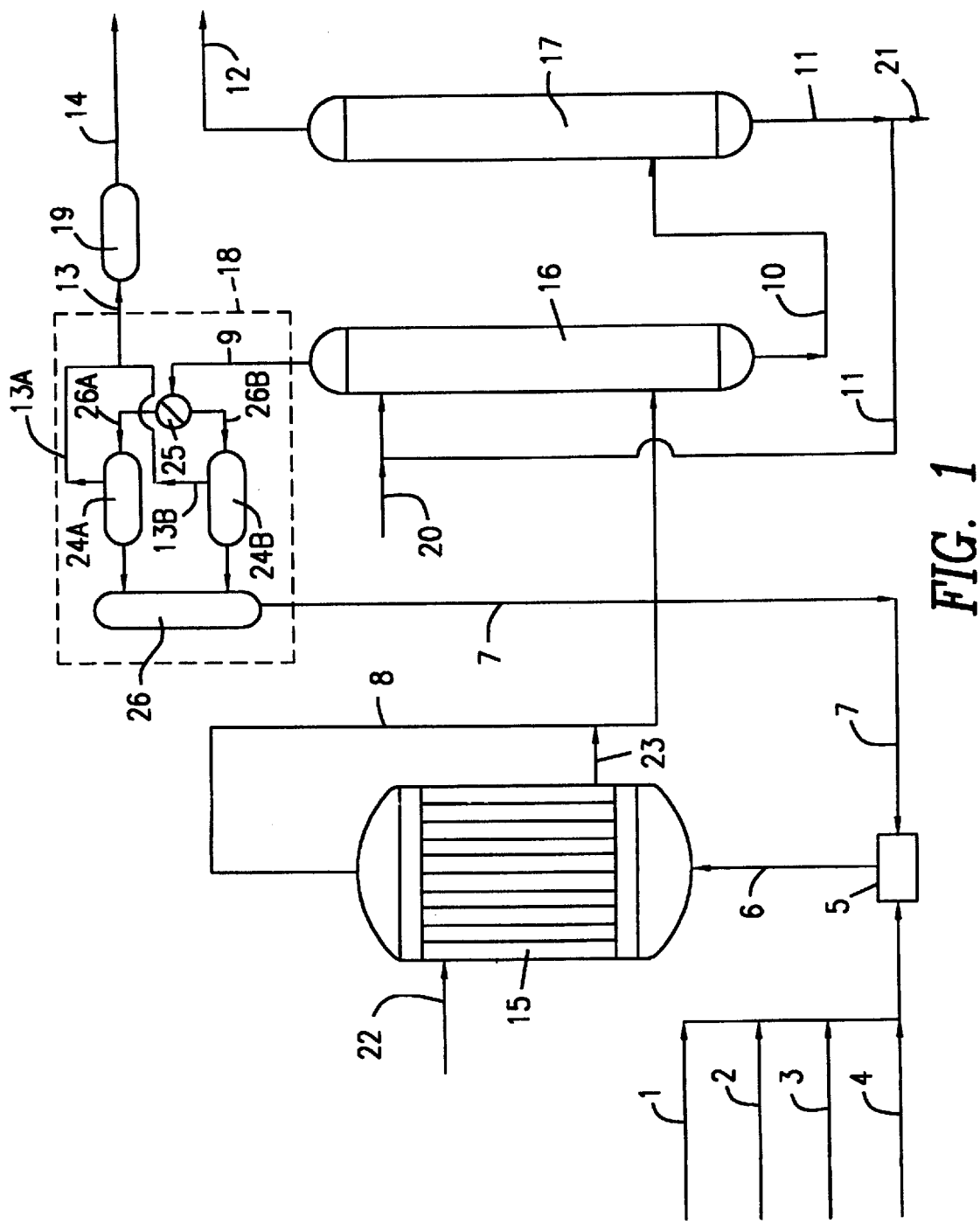
FIG. 1 is a flow sheet illustrating an embodiment of a method for the production of maleic anhydride according to this invention.

The first feature of this invention resides in causing the raw material gas which comprises an aliphatic hydrocarbon of not less than four nitrogen atoms, molecular oxygen, nitrogen, and an inert gas possessing a thermal conductivity of not less than 800 $(10^{-4} Wm^{-1} K^{-1})$ at 700 K to contact a vanadium-phosphorus oxide catalyst. While this vanadium-phosphorus oxide catalyst basically has the composition of divanadyl pyrophosphate, $(VO)_2 P_2 O_7$, but it is not limited to this composition, it is allowed to vary suitably the catalyst composition thereof, the atomic ratio of vanadium to phosphorus, the structure of divanadyl pyrophosphate (such as, for example, the choice of form among the $\alpha$, $\beta$, and $\gamma$ types), and the method of activation. Any of the vanadium-phosphorus oxide catalysts which are generally used or known to be usable for the production of maleic anhydride-can be used. The vanadium-phosphorus oxide catalyst to be used in this invention, therefore, is allowed to contain metals for the purpose of promoting a reaction. It may be used as deposited on such a carrier as silica or alumina.

As a typical example of the catalyst, a vanadium-phosphorus oxide catalyst intermediate which is characterized, as disclosed in JP-A-59-132,938, by exhibiting in the X-ray diffraction spectrum (anticathode Cu-K$\alpha$) main peaks at diffraction angles, $2\theta$ ($\pm 0.2°$), of 10.7°, 13.1°, 21.4°, 24.6°, 28.4°, and 29.5° may be cited. This catalyst, produced by a procedure which is characterized by comprising the steps of (a) causing a vanadium compound such as, for example, vanadium pentoxide to react with a phosphorus compound such as, for example, ortho-phosphoric acid and hydrazine as a reducing agent in an aqueous medium under such conditions that the atomic ratio of phosphorus to vanadium may fall in the range of 0.7–1.25:1 and the valency of vanadium in the range of 3.9–4.4 thereby inducing precipitation of the catalyst intermediate composition mentioned above, (b) extracting the precipitate from the aqueous medium, (c) heat-treating the precipitate in an organic medium in the presence of a phosphorus compound at a temperature in the range of 50°–200° C. thereby obtaining a catalyst precursor, (d) extracting the precursor from the organic medium, and then (e) calcining the precursor at a temperature in the range of 250°–550° C., has a composition in which the atomic ratio of phosphorus to vanadium in the range of 1–1.25:1.

EP-A-97105316.0 discloses a vanadium-phosphorus oxide which exhibits in the X-ray diffraction spectrum (anticathode Cu-K$\alpha$) main peaks at diffraction angles, $2\theta$ ($\pm 0.2°$), of 18.5°, 23.0°, 28.4°, 29.9°, and 43.1° and a ratio of intensity of the peaks at diffraction angles, $2\theta$ ($\pm 0.2°$), of 23.0° and 28.4° in the following range.

$0.3 \leq I (23.0)/I (28.4) \leq 0.7$ wherein I (23.0) and I (28.4) respectively denote peak intensities at the diffraction angles $2\theta$ ($\pm 0.2°$) of 23.0° and 28.4°.

The range is preferably $0.35 \leq I (23.0)/I (28.4) \leq 0.65$ and more preferably $0.4 \leq I (23.0)/I (28.4) \leq 0.6$. The atomic ratio of vanadium/phosphorus is 1/0.9–1/1.2, preferably 1/0.95–1/1.1.

As typical examples of the aliphatic hydrocarbon of not less than 4, preferably 4–8, carbon atoms, n-butane, 1-butene, 2-butene, butadiene, and mixtures thereof may be cited. This n-butane is allowed to contain propane, pentene, etc. in a small amount. The standard industrial grade n-butane can be used herein.

As typical examples of the inert gas possessing a thermal conductivity of not less than 800 $(10^{-4} Wm^{-1} K^{-1})$ at 700 K (hereinafter referred simply as "inert gas"), helium (2800 $(10^{-4} Wm^{-1} K^{-1})$), neon (880 $(10^{-4} Wm^{-1} K^{-1})$), etc. may be cited. These inert gases may be used either singly or in the form of a mixture. Among other inert gases, helium proves particularly advantageous.

The total concentration of nitrogen and the inert gas in the raw material gas is generally in the range of 60–94.5% by volume, preferably in the range of 75–90% by volume. The ratio of nitrogen to the inert gas [molar ratio of nitrogen/inert gas] is generally in the range of 0.05/1–1/1, preferably in the range of 0.05/1–0.6/1.

The concentration of the aliphatic hydrocarbon of not less than 4 carbon atoms in the raw material gas is generally in the range of 0.5–10% by volume, preferably 1–5% by volume in the case of n-butane, for example. The concentration of the molecular oxygen in the raw material gas is generally in the range of 5–50% by volume, preferably in the range of 10–25% by volume. As the source for the molecular oxygen, air is generally used.

The reaction conditions for the oxidation in this invention are not particularly restricted. The oxidation can be carried out under the conditions generally adopted or known to be adopted for the production of maleic anhydride excepting nitrogen and the inert gas are present in the raw material gas.

As regards the mode of reaction, the oxidation may be carried out in the fixed-bed system or the fluidized-bed system, whichever fits the occasion better. In the case of the oxidation in the fixed-bed system, for example, the reaction temperature is generally in the range of 300°–550° C., preferably in the range of 300°–450° C. The reaction pressure may be either normal pressure or an increased pressure. It is generally proper to carry out the reaction under normal pressure. The space velocity (STP) is generally in the range of 500–10,000 $hr^{-1}$ and preferably in the range of 1,000–5,000 $hr^{-1}$.

The second feature of this invention resides in a method for the activation of a vanadium-phosphorus oxide catalyst, which method comprises activating the vanadium-phosphorus oxide catalyst with a gas composition containing an inert gas possessing a thermal conductivity of not less than 800 $(10^{-4} Wm^{-1} K^{-1})$ at 700 K.

The inert gas-containing gas composition mentioned above is preferred to contain additionally nitrogen gas. The total concentration of nitrogen and the inert gas in the aforementioned gas composition is generally in the range of 60–94.5% by volume and preferably in the range of 75–90% by volume. The ratio of nitrogen to the inert gas [molar ratio of nitrogen/inert gas] is generally in the range of 0.05/1–1/1 and preferably in the range of 0.05/1–0.6/1.

The aforementioned gas composition is preferred to contain an aliphatic hydrocarbon of not less than 4 carbon atoms as the raw material for the production of maleic anhydride and molecular oxygen.

The kind, concentration, and composition of the aliphatic hydrocarbon of not less than 4 carbon atoms are as described above.

In this invention, the method for the activation of a vanadium-phosphorus oxide catalyst is executed by heat-treating a stream of the aforementioned gas composition in a reaction tube or a calcination oven packed with the catalyst. The heat treatment is generally carried out by causing the gas composition to flow through the reaction tube packed with the catalyst at a temperature in the range of 300°–600° C., preferably in the range of 350°–550° C., at a space velocity (SV) in the range of 500–10,000 $hr^{-1}$, preferably in the range of 1,000–3,000 $hr^{-1}$, for a period in the range of 5–200 hours, preferably in the range of 10–100 hours.

The third feature of this invention resides in causing a raw material gas containing an aliphatic hydrocarbon of not less then 4 carbon atoms, molecular oxygen, nitrogen, and an inert gas possessing a thermal conductivity of not less than 800 $(10^{-4}Wm^{-1}K^{-1})$ at 700 K to contact a vanadium-phosphorus oxide catalyst, effecting catalytic oxidation of the hydrocarbon, then separating and recovering the inert gas, and putting the recovered inert gas to use again. While this vanadium-phosphorus oxide catalyst basically has the composition of divanadyl pyrophosphate, $(VO)_2P_2O_7$, it is allowed to vary suitably the catalyst composition thereof, the atomic ratio of vanadium to phosphorus, the structure of divanadyl pyrophosphate (such as, for example, the choice of form among the α, β, and γ types), and the method of activation. Any of the vanadium-phosphorus oxide catalysts which are generally used or known to be usable for the production of maleic anhydride can be used. The vanadium-phosphorus oxide catalyst to be used in this invention, therefore, is allowed to contain such metals as are known to be added for the purpose of promoting a reaction.

As typical examples of the vanadium-phosphorus oxide catalyst, those which are enumerated above may be cited.

Now, one mode of embodying the method of this invention will be described below by reference to the accompanying drawing.

As illustrated in FIG. 1, an inert gas such as, for example, helium possessing a thermal conductivity of not less than 800 $(10^{-4}Wm^{-1}K^{-1})$ at 700 K is supplied through a conduit 1, molecular oxygen through a conduit 2, nitrogen gas through a conduit 3, and an aliphatic hydrocarbon of not less than 4 carbon atoms such as, for example, n-butane through a conduit 4 into a reaction gas mixing device S. In the reaction gas mixing device 5, the components mentioned above and a recovered inert gas such as, for example, helium introduced therein through a conduit 7 are mixed and adjusted to a prescribed reaction inlet gas concentration. This reaction inlet gas of the adjusted concentration is supplied through a conduit 7 to an oxidation reaction device 15.

The oxidation reaction device 15 does not impose any particular restriction. When it is in the form of the fixed-bed system, for example, a shell-and-tube type reactor is used. The tubes of this reactor which are packed with a prescribed amount of the catalyst are retained at a prescribed reaction temperature by being supplied with heat and deprived of heat owing to the circulation of a heating medium supplied through a conduit 22 and discharged through a conduit 23. The aliphatic hydrocarbon of not less than 4 carbon atoms such as, for example, n-butane which is the raw material is oxidized in the presence of the catalyst inside the oxidation reaction device 15. The gaseous effluent of this device 15 is passed through the conduit 8 and supplied to an absorption column 16. This gaseous effluent inside the absorption column 16 is absorbed by a solvent which is supplied through a conduit 20 and circulated through a conduit 11.

Further, as a method for recovering maleic anhydride from the produced oxidation reaction gas, an absorption method using a solvent or water as an absorbent, a solid recovering mathod for recovering the maleic anhydride as solid, and a recovering method combining these method are known. The recovering method for recovering maleic anhydride in accordance with the present invention is not specifically limited, and recovering methods which is usually adopted in the production of maleic anhydride or know to be adopted can be used.

The stream of maleic anhydride/solvent is passed through a conduit 10 to a stripping column 17. The crude maleic anhydride which is stripped within the stripping column 17 is passed through a conduit 12 and led to a purification device (not shown). The bottoms which remains in the stripping column 17 after the separation of the crude maleic anhydride is passed through the conduit 11 and circulated to the absorption column 16. Part of the bottoms is discharged from the system via a conduit 21.

The waste gas which has been deprived of the greater part of the maleic anhydride inside the absorption column 16 is released via the column top, passed through the conduit 9, and supplied to an inert gas separating device 18. The inert gas separating device 18, for example, is composed of a switching device 25 connected to the conduit 9, conduits 26A and 26B, and inert gas separators 24A and 24B connected thereto. It is enabled by the switching device 25 to communicate first with the first inert gas separator 24A.

The inert gas which is separated in the first inert gas separator 24B is transferred to a storage tank 26 and then forwarded through the conduit 7 to a reaction gas mixing device 5. The gas which has been deprived of the inert gas mentioned above is composed mainly of carbon monoxide, carbon dioxide, unaltered aliphatic hydrocarbon, oxygen, and nitrogen. This mixed gas is transferred through a conduit 13a and a conduit 13 to a waste gas burner 19, burnt therein, and discharged from the system through a conduit 14. Meanwhile, when the first inert gas separator 24A has been saturated, the switching device 25 is turned so that the mixed gas may be passed through the conduit 26B and treated similarly in the second inert gas separator 24B. The inert gas consequently separated and recovered is passed through the storage tank 26 and transferred to the reaction gas mixing device 5. The waste gas deprived of the inert gas is passed through the conduit 13B and transferred to a waste gas burner 19.

Incidentally, the inert gas separators 24A and 24B mentioned above are devices which are operated by such heretofore known method as the low temperature separation method, the membrane separation method, or the pressure oscillation adsorption separation methods They are allowed to adopt a combination of two or more such methods. The inert gas separators, when necessary, is allowed to be additionally furnished with a separating device capable of recovering the unaltered aliphatic hydrocarbon, oxygen, etc. so that these gases may be recovered and then used as mixed with the raw material gas.

Now, this invention will be described more specifically below by reference to working examples and controls. The conversion, selectivity, and yield indicated in these working examples and controls are based on the following definitions.

Conversion (mol. %)=[(Number of mols of n-butane consumed in the reaction)/(number of mols of n-butane supplied)]×100

Selectivity (mol. %)=[(Number of mols of maleic anhydride formed by the reaction)/(number of mols of n-butane supplied)]×100

Yield (mol. %) =[(Number of mols of maleic anhydride formed by the reaction)/(number of mols of butane supplied)]×100

Preparation of Catalyst (Catalyst-I)

In 4000 ml of benzyl alcohol, 400 g of vanadium pentoxide ($V_2O_5$) was suspended and reduced for 5 hours by being stirred and heated at 120° C. A phosphoric acid solution was prepared by dissolving 435.4 g of 99% orthophosphoric acid in 1000 ml of benzyl alcohol. When the reduced vanadium solution and the phosphoric acid solution were combined and heated at 120° C. and stirred at this temperature for 10 hours, a dark blue precipitate was formed. The reaction slurry consequently obtained was left cooling. The precipitate formed therein was separated, washed with acetone, and dried at 140° C. for 12 hours. The dried precipitate was molded in cylinders, 5 mm in length and 5 mm in diameter. A catalyst-I was obtained by calcining the cylinders in a stream of air at 480° C. for 4 hours.

(Catalyst-II)

In 4000 ml of isobutyl alcohol, 400 g of vanadium pentoxide ($V_2O_5$) was suspended and reduced for 10 hours by being stirred and heated at 105° C. A phosphoric acid solution was prepared by dissolving 435.4 g of 99% orthophosphoric acid in 1000 ml of isobutyl alcohol. When the reduced vanadium solution and the phosphoric acid solution were combined and heated at 105° C. and stirred at this temperature for 10 hours, a dark blue precipitate was formed. The reaction slurry consequently obtained was left cooling. The precipitate formed therein was separated, washed with acetone, and dried at 140° C. for 12 hours. The dried precipitate was molded in cylinders, 5 mm in length and 5 mm in diameter. A catalyst-II was obtained by calcining the cylinders in a stream of air at 500° C. for 4 hours.

(Catalyst-III)

In 5000 ml of distilled water, 3500 g of 85% orthophosphoric acid was heated to and kept at 80° C. and then 400 g of vanadium pentoxide ($V_2O_5$) was added thereto. When they were stirred and refluxed for 12 hours, a yellow precipitate was formed. The precipitate was separated, washed with acetone, and then dried at room temperature. When the dried precipitate and 4000 ml of 2-butyl alcohol added thereto were together heated to 80° C. and stirred at this temperature for 12 hours, a blue precipitate was formed. The resultant reaction slurry was left cooling. The precipitate consequently formed was separated, washed with acetone, and dried at 140° C. for 12 hours. The dried precipitate was molded in cylinders, 5 mm in length and 5 mm in diameter. A catalyst-III was obtained by calcining the cylinders in a stream of air at 500° C. for 4 hours.

(Catalyst-IV)

In 5000 ml of distilled water, 507 g of 85% orthophosphoric acid and 310 g of hydroxylamine hydrochloride added thereto were heated to and kept at 80° C. To the resultant hot solution, 400 g of vanadium pentoxide ($V_2O_5$) was added piecemeal attentively so as to avoid effervescence. When they were stirred and refluxed for 12 hours, a dark blue precipitate was formed. The resultant reaction slurry was left cooling. The precipitate consequently formed was separated, washed with acetone, and dried at 140° C. for 12 hours. The dried precipitate was molded in cylinders, 5 mm in length and 5 mm in diameter. A catalyst-IV was obtained by firing the cylinders in a stream of air at 520° C. for 4 hours.

EXAMPLES 1–12 and Controls 1–12

Condition 1

A flow reactor was packed with 10 g of a given catalyst. A mixed gas containing n-butane at a concentration of 1.5% by volume, oxygen at a concentration of 20% by volume, nitrogen at a concentration of 20% by volume, and helium at a concentration of 58.5% by volume was supplied at a space velocity of 1000 $hr^{-1}$ to the reactor, subjected to an activating treatment at 480° C. for 12 hours, and then allowed to induce gas phase oxidation of n-butane at a reaction temperature exhibiting the maximum yield.

Condition 2

A flow reactor was packed with 10 g of a given catalyst. A mixed gas of air containing n-butane at a concentration of 1.5% by volume was supplied to the reactor at a space velocity of 1000 $hr^{-1}$ and subjected to an activating treatment at 480° C. for 20 hours. Thereafter, a mixed gas containing n-butane at a concentration of 1.5% by volume, oxygen at a concentration of 20% by volume, nitrogen at a concentration of 2%, and helium at a concentration of 58.5% by volume was supplied to the reactor at a space velocity of 1000 $hr^{-1}$ and allowed to induce gas phase oxidation of n-butane at a reaction temperature exhibiting the maximum yield.

Condition 3

A flow reactor was packed with 10 g of a given catalyst. A mixed gas containing n-butane at a concentration of 1.5% by volume, oxygen at a concentration of 20% by volume, nitrogen at a concentration of 20% by volume, and neon at a concentration of 58.5% by volume was supplied at a space velocity of 1000 $hr^{-1}$ to the reactor, subjected to an activating treatment at 480° C. for 12 hours, and then allowed to induce gas phase oxidation of n-butane at a reaction temperature exhibiting the maximum yield.

Condition 4

A flow reactor was packed with 10 g of a given catalyst. A mixed gas containing n-butane at a concentration of 1.5% by volume, oxygen at a concentration of 20% by volume, nitrogen at a concentration of 20% by volume, and argon at a concentration of 58.5% by volume was supplied at a space velocity of 1000 $hr^{-1}$ to the reactor, subjected to an activating treatment at 480° C. for 12 hours, and then allowed to induce gas phase oxidation of n-butane at a reaction temperature exhibiting the maximum yield.

Condition 5

A flow reactor was packed with 10 g of a given catalyst. A mixed gas containing n-butane at a concentration of 1.5% by volume, oxygen at a concentration of 20% by volume, nitrogen at a concentration of 20% by volume, and methane at a concentration of 58.5% by volume was supplied at a space velocity of 1000 $hr^{-1}$ to the reactor, subjected to an activating treatment at 480° C. for 12 hours, and then allowed to induce gas phase oxidation of n-butane at a reaction temperature exhibiting the maximum yield.

Condition 6

A flow reactor was packed with 10 g of a given catalyst. A mixed gas of air containing n-butane at a concentration of 1.5% by volume was supplied to the reactor at a space velocity of 1000 $hr^{-1}$, subjected to an activating treatment at 480° C. for 20 hours, and allowed to induce gas phase oxidation of n-butane at a reaction temperature exhibiting the maximum yield.

The results of the experiment mentioned above are shown in Table 1.

TABLE 1

| Catalyst No. | Reaction conditions | (Gas added) | Reaction temperature (° C.) | Conversion of n-butane (mol. %) | Yield of MAN (mol. %) | Selectivity of MAN (mol. %) |
|---|---|---|---|---|---|---|
| Example 1 | Catalyst-I | Condition-1 | He | 370 | 84.9 | 60.1 | 70.8 |
| Example 2 | | Condition-2 | He | 380 | 82.1 | 56.1 | 68.3 |
| Example 3 | | Condition-3 | Ne | 370 | 84.5 | 57.6 | 68.2 |
| Control 1 | | Condition-4 | Ar | 385 | 82.1 | 50.1 | 61.0 |
| Control 2 | | Condition-5 | $CH_4$ | 385 | 83.1 | 50.5 | 60.8 |
| Control 3 | | Condition-6 | AIR | 385 | 84.7 | 50.2 | 59.3 |
| Example 4 | Catalyst-II | Condition-1 | He | 385 | 85.6 | 57.5 | 67.2 |
| Example 5 | | Condition-2 | He | 390 | 83.1 | 54.8 | 67.9 |
| Example 6 | | Condition-3 | Ne | 385 | 85.0 | 56.9 | 66.9 |
| Control 4 | | Condition-4 | Ar | 395 | 81.0 | 48.1 | 59.4 |
| Control 5 | | Condition-5 | $CH_4$ | 390 | 80.3 | 49.0 | 61.0 |
| Control 6 | | Condition-6 | AIR | 395 | 80.1 | 49.5 | 61.8 |
| Example 7 | Catalyst-III | Condition-1 | He | 385 | 84.1 | 58.1 | 69.1 |
| Example 8 | | Condition-2 | He | 395 | 82.0 | 55.3 | 67.4 |
| Example 9 | | Condition-3 | Ne | 385 | 84.6 | 56.5 | 66.8 |
| Control 7 | | Condition-4 | Ar | 400 | 81.0 | 48.2 | 59.5 |
| Control 8 | | Condition-5 | $CH_4$ | 405 | 83.0 | 48.5 | 58.4 |
| Control 9 | | Condition-6 | AIR | 400 | 81.5 | 48.7 | 59.8 |
| Example 10 | Catalyst-VI | Condition-1 | He | 405 | 78.0 | 56.0 | 71.8 |
| Example 11 | | Condition-2 | He | 415 | 80.1 | 53.8 | 67.2 |
| Example 12 | | Condition-3 | Ne | 405 | 79.1 | 54.1 | 68.4 |
| Control 10 | | Condition-4 | Ar | 415 | 79.3 | 49.0 | 61.8 |
| Control 11 | | Condition-5 | $CH_4$ | 415 | 78.3 | 48.7 | 62.2 |
| Control 12 | | Condition-6 | AIR | 420 | 78.0 | 48.5 | 62.2 |

*MAN: Maleic anhydride

EXAMPLES 13–20 and Controls 13–16

Condition 7

A flow reactor was packed with 10 g of a given catalyst. A mixed gas containing n-butane at a concentration of 1.5% by volume, oxygen at a concentration of 20% by volume, nitrogen at a concentration of 20% by volume, and helium at a concentration of 58.5% by volume was supplied to the reactor at a space velocity of 1000 $hr^{-1}$. The reactor was heated from 400° C. to 450° C. at a temperature increasing rate of 1° C./minute to effect an activating treatment at 450° C. for 20 hours and then gas phase oxidation of n-butane at a reaction temperature exhibiting the maximum yield.

Condition 8

A flow reactor was packed with 10 g of a given catalyst. A mixed gas of air containing N-butane at a concentration of 1.5% by volume was supplied to the reactor at a space velocity of 1000 $hr^{-1}$. The reactor was heated from 400° C. to 450° C. at a temperature increasing rate of 1° C./minute to effect an activating treatment at 450° C. for 12 hours and then gas phase oxidation of n-butane at a reaction temperature exhibiting the maximum yield.

Condition 9

A flow reactor was packed with 10 g of a given catalyst. A mixed gas containing n-butane at a concentration of 1.5% by volume, oxygen at a concentration of 20% by volume, nitrogen at a concentration of 20% by volume, and helium at a concentration of 58.5% by volume was supplied to the reactor at a space velocity of 1000 $hr^{-1}$. The reactor was heated from 400° C. to 450° C. at a temperature increasing rate of 1° C./minute to effect an activating treatment at 480° C. for 12 hours. Then, a mixed gas of air containing n-butane at a concentration of 1.5% by volume was supplied to the reactor at a space velocity of 100 $hr^{-1}$ and left reacting therein. It was allowed to induce gas phase oxidation of n-butane at a reaction temperature exhibiting the maximum yield.

The results of the experiments mentioned above are shown in Table 2.

TABLE 2

| Catalyst No. | Reaction conditions | Reaction temperature (° C.) | Conversion of n-butane (mol. %) | Yield of MAN (mol. %) | Selectivity of MAN (mol. %) |
|---|---|---|---|---|---|
| Example 13 | Catalyst I | Condition-7 | 365 | 65.1 | 60.6 | 71.2 |
| Control 13 | | Condition-8 | 385 | 84.7 | 50.2 | 59.3 |
| Example 14 | | Condition-9 | 370 | 79.5 | 57.1 | 71.8 |
| Example 15 | Catalyst II | Condition-7 | 380 | 84.1 | 57.1 | 67.9 |
| Control 14 | | Condition-8 | 395 | 80.1 | 48.5 | 60.5 |
| Example 16 | | Condition-9 | 385 | 81.1 | 54.1 | 66.7 |
| Example 17 | Catalyst III | Condition-7 | 380 | 86.0 | 58.9 | 68.5 |
| Control 15 | | Condition-8 | 400 | 81.5 | 48.7 | 59.8 |
| Example 18 | | Condition-9 | 385 | 83.1 | 55.9 | 67.3 |
| Example 19 | Catalyst IV | Condition-7 | 400 | 82.0 | 56.5 | 68.9 |
| Control 16 | | Condition-8 | 420 | 78.0 | 48.5 | 62.2 |
| Example 20 | | Condition-9 | 410 | 78.2 | 54.0 | 69.1 |

*MAN: Maleic anhydride

EXAMPLE 21

The gas compositions per cubic meter of Catalyst-I at main steps of process in the production of maleic anhydride by the use of Catalyst-I in an apparatus illustrated in FIG. 1 are shown in Table 3.

The reaction temperature, the conversion of n-butane, yield of maleic anhydride, and selectivity of maleic anhydride at the outlet of the reactor and the recovery ratio of helium by the production process are also shown.

Control 17

The gas compositions per cubic meter of Catalyst-I at main steps of the process of the production which omitted use of helium as the reaction gas by way of control are shown in Table 4.

TABLE 3

|  | Supply of new gas | Gas at the inlet to the reactor (6) | | Gas at the outlet of the reactor (8) | | Waste gas from the absorbing device (9) | | Recovered helium tube (7) | |
|---|---|---|---|---|---|---|---|---|---|
|  | (mol/hr) | mol/hr | mol. % | mol/hr | mol. % | mol/hr | mol. % | mol/hr | mol. % |
| n-butane | 1339.3 | 1339.3 | 1.50 | 225.0 | 0.25 | 225.0 | 0.25 | 0.2 | 0.00 |
| $O_2$ | 17857.1 | 17857.1 | 20.00 | 13370.1 | 14.79 | 13370.1 | 14.92 | 13.4 | 0.02 |
| CO | — | 0.0 | 0.00 | 569.6 | 0.63 | 569.6 | 0.64 | 0.6 | 0.00 |
| $CO_2$ | — | 0.0 | 0.00 | 592.9 | 0.66 | 592.9 | 0.66 | 0.6 | 0.00 |
| $H_2O$ | — | 0.0 | 0.00 | 4747.8 | 5.25 | 4747.8 | 5.30 | 4.7 | 0.01 |
| MAN | — | 0.0 | 0.00 | 823.7 | 0.91 | 24.7 | 0.03 | 0.0 | 0.00 |
| $N_2$ | 8928.6 | 8928.6 | 10.00 | 8928.6 | 9.87 | 8928.6 | 9.96 | 8.9 | 0.02 |
| He | 3058.0 | 61160.7 | 68.50 | 61160.7 | 67.64 | 61160.7 | 68.24 | 58102.7 | 99.95 |
| Total | 31183.0 | 89285.7 | 100.00 | 90418.3 | 100.00 | 89619.3 | 100.00 | 58131.1 | 100.00 |
| Temperature at an oxidation reactor (° C.) | | | | | | | | 400 | |
| Conversion of n-butane at the outlet of the oxidizing reactor (mol. %) | | | | | | | | 83.2 | |
| Yield of maleic anhydride at the outlet of the oxidizing reactor (mol. %) | | | | | | | | 61.5 | |
| Selectivity of maleic anhydride at the outlet of the oxidizing reactor (mol. %) | | | | | | | | 73.9 | |
| Ratio of recovery of helium in the separation refining device (mol. %) | | | | | | | | 95.0 | |

*MAN Maleic anhydride

TABLE 4

|  | Supply of new gas | Gas at the inlet to the reactor (6) | | Gas at the outlet of the reactor (8) | | Waste gas from the absorbing device (9) | | Recovered helium tube (7) | |
|---|---|---|---|---|---|---|---|---|---|
|  | (mol/hr) | mol/hr | mol. % | mol/hr | mol. % | mol/hr | mol. % | mol/hr | mol. % |
| n-butane | 1339.3 | 1339.3 | 1.50 | 247.8 | 0.27 | 247.8 | 0.28 | 0.0 | 0.00 |
| $O_2$ | 18392.9 | 18392.9 | 20.60 | 13733.9 | 15.15 | 13733.9 | 15.26 | 0.0 | 0.00 |
| CO | — | 0.0 | 0.00 | 813.7 | 0.90 | 813.7 | 0.90 | 0.0 | 0.00 |
| $CO_2$ | — | 0.0 | 0.00 | 847.0 | 0.93 | 847.0 | 0.94 | 0.0 | 0.00 |
| $H_2O$ | — | 0.0 | 0.00 | 4781.2 | 5.27 | 4781.2 | 5.31 | 0.0 | 0.00 |
| MAN | — | 0.0 | 0.00 | 676.3 | 0.75 | 20.3 | 0.02 | 0.0 | 0.00 |
| $N_2$ | 69553.5 | 69553.6 | 77.90 | 69553.6 | 76.72 | 69553.6 | 77.28 | 0.0 | 0.00 |
| He | 0.0 | 0.0 | 0.00 | 0.0 | 0.00 | 0.0 | 0.00 | 0.0 | 0.00 |
| Total | 89285.7 | 89285.7 | 100.00 | 90653.5 | 100.00 | 89997.5 | 100.00 | 0.0 | 0.00 |
| Temperature at an oxidation reactor (° C.) | | | | | | | | 420 | |
| Conversion of n-butane at the outlet of the oxidizing reactor (mol. %) | | | | | | | | 81.5 | |
| Yield of maleic anhydride at the outlet of the oxidizing reactor (mol. %) | | | | | | | | 50.5 | |
| Selectivity of maleic anhydride at the outlet of the oxidizing reactor (mol. %) | | | | | | | | 62.0 | |
| Ratio of recovery of helium in the separation refining device (mol. %) | | | | | | | | 0.0 | |

*MAN: Maleic anhydride

The entire disclosure of Japanese Patent Application No. 10-36198 filed on Feb. 18, 1998, including specification, claims, summary and drawing are incorporated herein by reference in its entirety.

What is claimed is:

1. A method for the production of maleic anhydride by the catalytic gas phase oxidation of a raw material gas containing an aliphatic hydrocarbon of not less than 4 carbon atoms and molecular oxygen with a vanadium-phosphorus oxide catalyst, characterized by said raw material gas allowing presence therein of nitrogen and an inert gas possessing a thermal conductivity of not less than 800 $(10^{-4} Wm^{-1} K^{-1})$ at 700 K wherein the total concentration of said nitrogen gas and said inert gas in said raw material gas is in the range of 60–94.5% by volume and wherein the ratio of nitrogen gas to said inert gas is in the range of 0.05/1–1/1.

2. The method according to claim 1, wherein said inert gas is at least one species of inert gas selected from the group consisting of helium and neon.

3. The method according to claim 1, wherein said inert gas is helium.

4. The method according to claim 1, wherein said aliphatic hydrocarbon of not less than 4 carbon atoms is n-butane.

5. The method of claim 1 comprising recovering the thus produced maleic anhydride from the gaseous reaction product by contact with an absorbent to provide a gaseous residue separating the inert gas from said gaseous residue and recycling said insert gas to become a component of said raw material gas.

6. A method according to claim 5, wherein said inert gas is at least one species of inert gas selected from the group consisting of helium and neon.

7. A method according to claim 5, wherein said inert gas is helium.

8. A method according to claim 5, wherein said aliphatic hydrocarbon of not less than 4 carbon atoms is n-butane.

9. A method for the activation of a vanadium-phosphorus oxide catalyst for the catalytic gas phase oxidation of a raw material gas containing an aliphatic hydrocarbon of not less than 4 carbon atoms with molecular oxygen comprising:

activating the vanadium-phosphorus oxide catalyst with a gas composition containing:

an inert gas possessing a thermal conductivity of not less than 800 $(10^{-4} Wm^{-1}K^{-1})$ at 700 K, nitrogen and an aliphatic hydrocarbon of not less than 4 carbon atoms and molecular oxygen.

10. A method according to claim 9, wherein said activating temperature is in the range of 300°–600° C.

* * * * *